US005763625A

United States Patent [19]

Boothman et al.

[11] Patent Number: 5,763,625
[45] Date of Patent: Jun. 9, 1998

[54] SYNTHESIS AND USE OF β-LAPACHONE ANALOGS

[75] Inventors: David A. Boothman; Benjamin J. Frydman; Donald T. Witiak, all of Madison, Wis.

[73] Assignee: Wisconsin Alumni Research Foundation, Madison, Wis.

[21] Appl. No.: 428,574

[22] Filed: Apr. 25, 1995

[51] Int. Cl.$^6$ ................................. C07D 311/80
[52] U.S. Cl. .................. 549/390; 549/391; 549/393; 549/395
[58] Field of Search ..................... 549/390, 391, 549/393, 395

[56] References Cited

FOREIGN PATENT DOCUMENTS

WO/94/04145   3/1994   WIPO.

OTHER PUBLICATIONS

Chemical Abstracts, vol. 110, No. 1, 1989; Columbus, OH, U.S.; abstract No. 88167h, D. Boothman et al.: Inhibition of Potentially Lethal DNA Damage Repair in Human Tumor Cells by Beta–Lapachone, an Activator of Topoisomerase I., p. 35; XP002007963; see Abstract & Cancer Res., vol. 49, No. 3, 1989, Engl., pp. 605–612.

Chemical Abstracts, vol. 91, No. 1, 1979; Columbus, OH, U.S.; abstract No. 151101p, R. Docampo et al.: Beta–Lapachone Enchancement of Lipid Peroxydation and Superoxide Anion and Hydrogen Peroxide Formation by Sarcoma 180 Ascites Tumor Cells, p. 25; Abstract only considered.

Chemical Abstracts, vol. 112, No. 1, 1990; Columbus, OH, U.S.; abstract No. 30301x, D. Boothman: Can a DNA Repair Inhibitor Block the Tumorigenic Transformation of Normal Cells Following a Genetic Insult?, p. 19, Abstract Only Considered.

Chemical Abstracts, vol. 122, No. 25, 1995; Columbus, OH, U.S.; abstract No. 309888w, I. Szumiel et al.: Effects of Topoisomerase I–Targeted Drugs on Radiation Response of L5178Y Sublines Differentially Radiation and Drug Sensitive, p. 460; Abstract Only Considered.

Chemical Abstracts, vol. 123, No. 1, 1995; Columbus, OH, U.S.; abstract No. 217883h, s. Planchon et al.: Beta–Lapachone Mediated Apoptosis in Human Promyelocytic Leukemia (HL–60) and Human Prostate Cancer Cells, p. 43; Abstract Only Considered.

Chemical Abstracts, vol. 123, No. 1, 1995; Columbus, OH, U.S.; abstract No. 217884j, Chiang Li et al.: Induction of Apoptosis by Beta–Lapachone in Human Prostate Caner Cells, p. 43; Abstract Only Considered.

Chemical Abstracts, vol. 78, No. 27, 1973; columbus, OH, U.S.; abstract No. 147733k, J. Mock et al.: Chemical Studies of the Proteaceae VI. Two Naphthoquinones from Stenocarpus Silignus, p. 361; Abstract Only Considered.

Chemical Abstracts, vol. 87, No. 7, 1977; Columbus, OH, U.S.; abstract No. 127264r, A. Pinto et al.: Schistosoma Mansoni: Blockage of Cercarial Skin Penetration by Chemical Agents. I. Naphthoquinones and Derivatives, p. 58; Abstract Only Considered.

Proc. Natl. Acad. Sci., U.S.A., vol. 86, No. 13, Jul. 1989, Washington, D.c., U.S., pp. 4963–4967, XP002007962, D. Boothman et al., Inhibition of Radiation Induced Neoplastic Transformation by HBeta–Lapachone, see pp. 4963–4966.

A. Ventura Pinto et al. Ci+e.cir +ee encia e culture, vol. 27 (supp), p. 165, 1975 (English translation attached).

Stacy Anderson, UW Prof Find Cancer Fighter, Capital Times, Mar. 20, 1995.

David A. Boothman et al., Posttreatment Exposure to Camptothecin Enhances the Lethal Effects of X–Rays on Radioresistant Human Malignant Melanoma Cells, Int. J. Radiation Oncology Biol. Phys. vol. 24, No. 5, pp. 939–918, 1992.

Chiang J. Li et al., Beta–Lapachone, a Novel DNA Topoisomerase I Inhibitor with a Mode of Action Different from Camptothecin. The Journal of Biol. Chem., vol. 268, No. 30, pp. 22463–22468, Oct. 25, 1993.

Solary et al. Differential Induction of Apoptosis in Undifferentiated and Differentiated HL–60 Cells by DNA Topoisomerase I and II Inhibitors, Blood, vol. 81, No. 5, pp. 1359–1368, Mar. 1, 1993.

Abstract #2630 Topoisomerase I Inhibitors Potentiate Raidation Lethality in vitro, Abstract Only Considered.

*Primary Examiner*—Johann Richter
*Assistant Examiner*—Jane C. Oswecki
*Attorney, Agent, or Firm*—DeWitt Ross & Stevens SC

[57] ABSTRACT

3-Substituted-β-lapachone analogs and their use either alone or to augment chemotherapy or radiotherapy to induce programmed neoplastic cell death without exhibiting toxicity to surrounding normal cells are disclosed. In particular, 3-allyl-β-lapachones, 3-alkyl-β-lapachones and 3-halo-β-lapachones were found to be Topoisomerase (Topo I) inhibitors. When these analogs are used alone there is a reversible single-strand break in the DNA of neoplastic cells causing apoptosis and cell death in some cells. However, when these analogs are combined with chemotherapy or X-irradiation, an irreversible Topo I-mediated break is achieved. A new and more efficient chemical synthesis of the compounds is also disclosed.

32 Claims, No Drawings

SYNTHESIS AND USE OF β-LAPACHONE ANALOGS

BACKGROUND OF THE INVENTION

X-irradiation and chemotherapy are used to eliminate neoplastic cells. It has been found that a chemical post-treatment with β-lapachone analogs after X-irradiation greatly enhanced the lethality of the radiation and/or chemotherapy and destroy more neoplastic cells. Specifically, the β-lapachone post-treatment irreversibly damages the DNA of the neoplastic cells.

DNA is structurally damaged in various ways by different chemical and physical agents. For example, damage following ionizing radiation includes single and double-strand DNA breaks, apurinic/apyrimidinic alkaline-labile sites, altered basis, and intra- and inter-strand DNA protein cross-links. The predominant DNA lesions occurring after X-irradiation are single and double-strand breaks, and the production of the latter lesions correlate well with cytotoxicity. Each type of DNA lesion may stimulate different cellular responses which activate or induce a variety of DNA repair pathways. Along with the repair stimulation following radiation, mammalian cells respond to damage by altering gene expression and inducing post-translational modifications of proteins, including phosphorylation and ADP-ribosylation.

If damaged DNA regions are not repaired by the cell's enzymatic systems, the results are lethal or cause genetic rearrangements, ultimately leading to cell transformation and cancer. Rapid and accurate repair systems are important not only for cell survival, but for preventing genetic alterations which may lead to carcinogenesis. These facts are corroborated by a variety of human cancer-prone diseases, which are thought to result from deficiencies in DNA repair. These groups of diseases include the xeroderma pigmentosum, ataxia telangiectasia (whose cells are hypersensitive to X-irradiation) and Bloom's syndrome.

Conversely, if DNA repair is deliberately blocked or altered via administration of inhibitors, the lethal effects of anti-neoplastic agents can be greatly enhanced, often without creating carcinogenic consequences. The possibility of improving chemotherapy by inhibiting DNA repair has been suggested and tested years ago. In these prior studies, the major DNA repair inhibitor was caffeine, which was proposed to inhibit post-replication repair. Although the results of these studies were promising, the extremely high concentrations of caffeine required to enhance radiotherapy or chemotherapy precluded their clinical utility.

Another class of DNA repair inhibitors proposed to enhance cancer chemotherapy were nicotinamide analogs, such as 3-aminobenzamide (3-ABA). These compounds were initially proposed to be ligase inhibitors, but were later found to be inhibitors of poly (ADP-ribose) transferase (ADPRT). These compounds, therefore, block ADP-ribosylation which would otherwise stimulate DNA repair complexes and auto-down-regulate ADPRT itself. DNA repair inhibition by 3-ABA was based on this activity. However, 3-ABA, along with other nicotinamide analogs, have not demonstrated significant clinical utility due to the fact that effective concentrations cannot be achieved.

β-lapachone is also a known inhibitor of cell survival after radiation because it is an inhibitor of DNA repair and Topoisomerase I. However, due to its extreme toxicity, this drug has not gained widespread use.

Camptothecin is also a well-known DNA-repair inhibitor. However, like β-lapachone, camptothecin and its derivatives are relatively toxic, causing lethality in healthy cells surrounding neoplastic sites. Consequently, many camptothecin derivatives of this compound have been synthesized to increase compound stability and water solubility. Camptothecin derivatives, as well as camptothecin itself, are not related to β-lapachone or its derivatives and inhibits Topoisomerase I by different mechanisms than β-lapachone. Also, camptothecin and its derivatives are hydrophobic, making them poor candidates for pharmaceutical or medical applications.

Until now, little has been done to exploit DNA repair pathways for chemotherapy or radiotherapy. Potential clinical utility exists for the development of drugs that modulate DNA repair enzymes and thereby enhance the lethality of DNA damaging agents. Novobiocin, an inhibitor of Topoisomerase II (Topo II), was useful as an adjunct to DNA damaging drugs. Pentoxiphylline, a caffeine analog, has been tested in phase I clinical trials and recent studies indicate that this compound, caffeine and other methylxanthines, blocks DNA repair by allowing damaged cells to prematurely enter mitosis. These drugs prevent $G_2$ arrest in damaged cells, a stage which presumably allows DNA repair before cell division.

Past data indicate that Topoisomerase I (Topo I) is somehow involved in DNA repair and is affected by the aforementioned DNA repair inhibitors and, therefore, represents a prime target for radio- or chemotherapy. Areas of the mammalian genome undergoing high rates of transcription have higher Topo I levels and repair faster. Topo I is an essential enzyme required for transcription and replication. Topo I unwinds supercoiled DNA by breaking and rejoining one DNA strand as the enzyme rotates about its axis and passes the other DNA strand through the break. Topo I thereby relieves physical stress in DNA caused by RNA transcription and DNA replication. Unlike Topo II, Topo I levels within the cell do not vary as cells progress through their replicative cycle. Topo I is present in equivalent levels in log-phase as well as in quiescent human cells, which makes this enzyme an ideal target for chemo- and/or radio-therapeutic approaches. Many current chemical therapeutic regimens are directed against logarithmically growing cells (i.e. cells in S-phase). If radio- and chemotherapeutic regimens can be developed that act upon non-cell cycle regulated enzymatic targets, resting as well as cycling tumor cells may be eliminated. This would aid in reducing resistance caused by recruitment of tumor cells from resting or hypoxic states.

Recent data indicates that Topo I inhibitors can cause a Topo I-mediated lesion modification of DNA in X-irradiated human cancer cells which were exposed to ionizing radiation. This Topo I mediated conversion of single-strand DNA breaks to double-strand breaks explains the radiation and chemotherapy synergy caused by β-lapachone derivatives. When Topo I binds to a plasmid containing a unique nick, the enzyme causes linearization of that substrate at an 800-fold greater rate compared to the enzyme's normal unwinding activity on intact DNA. Single-strand DNA regions or breaks are initially created by X-irradiation. Considerable evidence has accumulated to indicate that both mammalian and bacterial Topo I enzymes bind very avidly to single-strand DNA sequences and neither camptothecin nor β-lapachone affect such initial enzyme binding. Topo I has a very high affinity for nicked or single-stranded gapped, double strand DNA. After non-specifically binding to nicked DNA, the enzyme cuts the DNA strand opposite the nick resulting in linearization of the DNA substrate. The rate of this reaction was far more rapid (increased by a factor of 800 to 1,000) than nicking/unwinding activities upon undamaged plasmid DNA. Thus, conversion of single-strand nicks into double-strand breaks by Topo I appears to be an extremely rapid and efficient reaction compared to the enzyme's actions upon intact undamaged double-stranded DNA.

The present hypothesis is that two pathways can exist for Topo I activity following radiation. First, a normal pathway in which down-regulation of the enzyme is required for DNA repair. The second pathway involves a β-lapachone-analog-enzyme mediated suicide pathway in which a Topo I modulator somehow prevents the enzyme's down-regulation and/or changes the enzyme's activity site such that it can still bind, create a double-strand DNA break from a single-strand break and cause covalent attachment of the enzyme to the DNA break in spite of being modified. This results in a synergistic cell-killing mechanism between β-lapachone derivatives and radiotherapy or chemotherapy. Recent data indicate that cells undergoing apoptosis (or programmed cell death) may irreversibly degrade poly (ADP) ribosyl transferase (ADPRT), a key enzyme required for DNA repair and for controlling (i.e. down-regulating) Topo I. Thus, the combination of loss of ADPRT and subsequent uncontrolled Topo I activity may contribute to cell death, possibly via apoptosis. Recent data indicate that all three substituted β-lapachone derivatives can cause apoptosis indicating the use of these compounds alone as chemotherapeutic agents; in particular, these agents should be effective against prostate, colon, lung, melanoma, and breast cancers due to the elevated Topo I enzyme levels in these tumors compared to normal cells.

After cells receive ionizing radiation, it appears that the DNA repair complex, which probably contains DNA ligase, DNA polymerase-β, and ADPRT, competes with Topo I and other proteins for available single-strand DNA damaged sites. Creation of double-strand DNA lesions from single-strand DNA breaks has been reported under normal repair conditions and may be the result of the cell's inability to efficiently down-regulate Topo I. Normally, after ionizing radiation, ADPRT/DNA binding and subsequent enzymatic activities increase. ADPRT acts to stabilize the break (ADPRT/DNA binding) and its ADP-ribosylation activity, which increases due to DNA binding, can stimulate DNA repair and down-regulate Topo I. This combined action by ADPRT functions to stabilize DNA lesions, out-competes Topo I for these sites, and prevents conversion of single-stranded breaks to double-stranded breaks by this down-regulation of Topo I. The temporary down-regulation of Topo I is needed, therefore, to repair single-strand breaks. After some time (approximately 60 minutes in human cells), Topo I activity recovers and its unwinding activity may be needed to repair other types of more persistent DNA damage, such as DNA protein cross-links, which can be induced by chemotherapeutic agents. In fact, Topo I inhibitors (such as camptothecin) have been used to augment cis-platin and melphalan cytotoxicities.

In the presence of a modulator of Topo I, such as the present invention of β-lapachone analogs, the processes of DNA repair is altered and DNA lesion modification by Topo I occurs. Somehow Topo I is no longer down-regulated by cellular increases in ADPRT in the presence of β-lapachone derivatives. The manner by which these compounds either prevent Topo I down-regulation or cause the enzyme to bind to single nicked DNA in spite of post-translational down-regulation is unknown, but recent convincing data demonstrates that the Topo I mediated DNA lesion modification process does occur. The present analogs appear to bind directly to the enzyme before it forms a complex with DNA. Therefore, these compounds inhibit Topo I directly in a very different mechanism than camptothecin derivatives, which only bind a Topo I-DNA intermediate. The overall effect of these Topo I modulators in combination with ionization radiation and/or chemotherapy is that the enzyme is able to bind to damaged DNA and create double-stranded irreversible DNA breaks, induced apoptosis, and kill log-phase as well as confluence arrested human tumor cells which have elevated Topo I levels (i.e., prostate, colon, breast, melanoma and lung cancers).

Only a few agents are known to modulate Topo I. The only known drugs that specifically inhibit Topo I are β-lapachone and its derivatives, camptothecin, Hoescht dyes, (which are weak inhibitors) and their respective analogs. Many have attempted to produce various camptothecin and β-lapachone analogs, since the parent drugs have strong toxic side effects at concentrations required for their use alone as chemotherapeutic agents. However, the present invention overcomes the strong cytotoxic effects of these parent compounds, is stabilized in air, water or human serum while still causing sufficient lethality alone or in combination with radiotherapy or chemotherapy against human neoplastic cells.

SUMMARY OF THE INVENTION

This invention relates to β-lapachone analogs, substituted at the biologically relevant C-3 position, and their use either alone or to augment radio- and chemotherapy to induce programmed neoplastic cell death.

These analogs work using two different mechanisms. First, these analogs can work synergistically with chemo- or radiotherapeutic agents augmenting their potential. Secondly, these analogs work via another mechanism as chemotherapeutic agents.

The β-lapachone analogs of the present invention are those having the following structure:

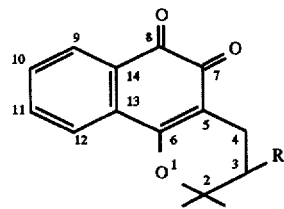

where R is $(CH_2)_n$-$R_1$ where n is an integer from 0–10 and $R_1$ is hydrogen, an alkyl, an aryl, a heteroaromatic, a heterocyclic, an aliphatic, an alkoxy, a hydroxy, an amine, a thiol, an amide, or a halogen.

Specifically, this invention relates to 3-substituted-β-lapachone derivatives particularly 3-hydroxy β-lapachone, 3-alkoxy-β-lapachones, 3-alkyl-β-lapachones and 3-halo-β-lapachones, and their synthesis as well as their use either alone as a chemotherapeutic agent or as an enhancer of the cytotoxic effects of DNA damaging agents (i.e. chemotherapy and radiotherapy). When these analogs are combined with radiation or some other DNA damaging agent which induces DNA strand cisions or cause alkylation damage, a double stranded irreversible break is achieved which results in lethality. These analogs of 3-lapachone require only about one tenth the dose necessary compared to lapachones. 3-Allyl-β-lapachone gives a drug enhanced radiation value (DER value) of 3.6, which is better than any camptothecin derivative (e.g. topotecan) which was administered at 10 times the dose of the 3-allyl-β-lapachone but resulted in a DER value of only 2.7. Therefore, the surrounding unirradiated tissues would not be affected nor would secondary tumors be induced (they may actually be prevented) in this unirradiated area when using the 3-allyl-β-lapachone.

The administration of efficacious doses of 3-allyl-β-lapachone to human lung, breast, melanoma, prostate, leukemia and colon cancer cells increases the lethal effects of radiation without causing toxicity to surrounding unirradiated normal cells. Tumor selectivity is afforded by elevations of Topo I in cancerous lung, colon, breast, melanoma, prostate and leukemia cells.

Not only does this invention identify and synthesize novel β-lapachone analogs and their anti-neoplastic use, but it discloses a new effective chemical synthesis of these compounds. This novel synthesis is superior over the prior art due to the fact that it produces analogs which are free of impurities and the process is reproducible.

Finally, another use of these 3-substituted β-lapachone derivatives is for the treatment of HIV infection, commonly known as AIDS. Inhibition of Topo I leads to a blockage of the HIV-related reverse transcriptase. The inhibition of reverse transcriptase using β-lapachone has been demonstrated, and it is proposed that the use of the 3-substituted β-lapachones will be for prolonging the survival of AIDs patients and treating their viral infections to prevent the spread of infected cells in the body via the Topo I-mediated inhibition of the HIV-related reverse transcriptase.

These analogs overcome the disadvantages of the prior art (i.e., β-lapachone and camptothecin) due to the fact that these β-lapachone analogs are not cytotoxic to unirradiated, healthy cells surrounding the neoplastic tumor site and require much lower dose levels for effectiveness.

Another improvement over the prior art is that several of these analogs are water soluble derivatives unlike β-lapachone itself and camptothecin. Thus, these analogs are suitable for medical administration and pharmaceutical products.

In addition, another aspect of this invention is the use of 3-substituted β-lapachones to induce programmed cell death. These 3-substituted derivatives, induce programmed cell death without the use of radiation or additional chemotherapy in cells having elevated Topoisomerase I levels such as cancerous lung, colon, breast, melanoma, prostate, and leukemia cells. Specifically, these cells induce cell death, inter alia, through apoptotic mechanisms. Thus, these analogs can be used as chemotherapeutic agents themselves.

DETAILED DESCRIPTION OF THE PREFERRED EMBODIMENT

I. Evidence of Down-Regulation of Topo I and 3-Substituted β-Lapachone I-Induced Topo I Mediated Suicide Pathway Leading to Lethality A. Down-Regulation of Topo I Activity In Normal and Neoplastic Chinese Hamster Embryo Fybroblasts.

To observe changes in Topo I levels with or without ionizing radiation as cells progress toward a neoplastic state, Topo I activities were measured in unirradiated or X-irradiated confluence-arrested normal diploid CHEF/18 cells and their neoplastic derivatives: 21-2, 21-2M3, and T30-4. CHEF cells were treated with 400 cGy, an equitoxic dose resulting in 20% survival for each cell type. Topo I activities of unirradiated and X-irradiated CHEF cells at 4 h posttreatment were assayed in 4 separate experiments. Topo I enzymatic and survival recovery data following radiation for all four cell types are summarized in Table 1.

TABLE 1

Down-Regulation of Topo I Activity in Normal and Neoplastic Chinese Hamster Embryo Fibroblast (CHEF) Cells.[1]

| Cell Type (Malignancy) | X-Ray Dose (cGy) | Topo I[1] Enzyme Activity | Extent of Topo I[2] Down-Regulation | % Survival[3] Enhancement |
|---|---|---|---|---|
| CHEF/18 (0/42)* | 0 | 4.0 ± 0.5 | 2X | 22 ± 2 |
|  | 400 | 2.0 ± 0.1 |  |  |
| 21-2 (0/42)* | 0 | 4.1 ± 1.0 | 3X | 25 ± 4 |
|  | 400 | 1.2 ± 0.04 |  |  |
| T30-4 (42/42)* | 0 | 11.4 ± 0.1 | 29X | 60 ± 7 |
|  | 400 | 4.0 ± 0.01 |  |  |
| 21-2M3 (18/42)* | 0 | 6.7 ± 0.1 | 10X | 45 ± 12 |
|  | 400 | 0.7 ± 0.02 |  |  |

[1]Topo I enzyme activity, defined as the loss of 60% supercoiled DNA substrate (i.e., 300 μg p36B4 plasmid) per mg protein per minute, for X-irradiated and unirradiated cells at 4 h post-irradiation was determined from the slope of the linear portion of the Topo I activity curves in FIGS. 2A through 2D (see Appendix. 13).
*Indicates number of tumors formed in nude mice (43).
[2]Extent of down-regulation of Topo I enzyme activity following 400 cGy was calculated by the ratio of Topo I enzyme activities of unirradiated to X-irradiated cells.
[3]Survival enhancement values for CHEF cells were previously determined using colony forming assays (33.42.43) by subtracting the survival of cells immediately following ionizing radiation (i.e., no posttreatment) from the survival of irradiated cells after 8 h recovery.

A gradual increase in Topo I activity was noted as cells progressed to neoplasia. When unirradiated CHEF/18 cells were compared to its neoplastic derivatives, higher enzyme activities in the order of: CHEF/18<21-2<212M3<T30-4 were found. Unirradiated T30-4 cells, the most malignant cell type, contained nearly 3-fold higher Topo I levels than unirradiated CHEF/18 cells. Following radiation, Topo I levels were dramatically down-regulated and the extent of down-regulation increased as cells became more neoplastic. Topo I down-regulation correlated with the capacity of damaged cells to recover from radiation; cells which recovered well from radiation damage also demonstrated a greater capacity to down-regulate Topo I (see Table 1).

Camptothecin, a specific Topo I inhibitor, was used to prove that Topo I and not Topo II activities were assayed. Extracts from unirradiated CHEF/18 cells and its neoplastic derivatives (i.e., 21-2M3 and T30-4) containing Topo I activities were inhibited 100% by camptothecin (50 nM-1 μM) at 30 minutes and 2 hours. Administration of lower levels of camptothecin (between 1 nM and 10 nM) resulted in partial inhibition of Topo I. Enzymatic activity was observed in controls and after administration of 500 nM m-AMSA, a potent Topo II inhibitor. Topo II levels were not detected in confluence-arrested human or CHEF/18 cells. This is consistent with previous results showing that Topo II is not present in quiescent cells.

B. Temporal Regulation of Topo I in X-irradiated CHEF Cells.

Topo I activity was investigated in CHEF cells after various times of recovery following radiation. Normal CHEF/18 and transformed 21-2M3 cells were unirradiated or X-irradiated (400 cGy) and incubated at 37° C. for various times. Topo I activity decreased in both CHEF/18 and 21-2M3 cells within 5 minutes and remained low for the next 12 hours. Topo I activities did not recover for nearly 18 hours after radiation, at which time only 75% control levels were noted. Topo I levels recovered completely in 24 hours.

C. Down-Regulation of Topo I Activities In Human Cells After Ionizing Radiation.

Topo I activity in human malignant melanoma (U1-Mel) cells was examined before and after X-irradiation. As in CHEF cells, Topo I activity decreased in X-irradiated U1-Mel cells within 5 minutes post-irradiation. The lowest Topo I level was noted at 45 minutes post-irradiation. Topo I activity in irradiated U1-Mel cells remained low until 65 minutes, when enzyme activity increased to roughly 80% unirradiated control levels. Unlike CHEF cells which took 24 hours for Topo I levels to recover, Topo I activity within X-irradiated U1-Mel cells returned to levels comparable to control cells within 65–120 minutes. We also examined Topo I activity in U1-Mel cells following various doses of ionizing radiation at 45 minutes. Topo I activity was gradually down-regulated by increasing doses of radiation up to 450 cGy. At doses of radiation greater than 450 cGy, Topo I activity remained at 1–2% control levels. Topo I down-regulation was observed in a variety of human normal and tumor cells following equitoxic doses of radiation giving 10% survival, with similar temporal down-regulation as noted in U1-Mel cells (see Table 2). Higher Topo I activities were noted in unirradiated human tumor (U1-Mel, HTB-152, and HEp-2) compared to human normal (GM2936B, GM2937A, and IMR-90) cells. Topo I activities in X-irradiated human tumor cells were, however, down-regulated to a greater extent than in human normal cells. In fact, Topo I levels following radiation decreased in X-irradiated human tumor cells to far lower levels than observed in irradiated normal cells (p<0.1, Student's t test). As in CHEF cells, the capacity to down-regulate Topo I after radiation correlated with enhanced survival in various human cells after radiation.

It is logical that if down-regulation of Topo I occurs in cells damaged by irradiation in order to repair incised DNA breaks, then cells whose DNA is damaged by chemotherapy will also down-regulate Topo I in the same manner; for example, it has been demonstrated that UV-irradiation also down-regulates Topo I. Furthermore, it has been demonstrated that presubstituted β-lapachone compounds will increase lethality alone (via apoptosis) and in combination with radiotherapy or chemotherapy by preventing Topo I down-regulation and causing the Topo I mediated suicide pathway discussed above and illustrated in Pathway 1.

TABLE 2

Decreased Topo I Activity Following Ionizing Radiation in Human Cells

| Cell Type | X-Ray Dose (cGy) | Topo I[1] Enzyme Activity | Extent of Topo I[2] Down-Regulation | % Survival[3] Enhancement |
|---|---|---|---|---|
| Tumor Cells | | | | |
| U1-Mel | 0 | 10.8 ± 0.4 | 23X | 45 ± 3.4 |
|  | 450 | 0.5 ± 0.05 | | |
| HTB-152 | 0 | 9.0 ± 0.2 | 23X | 25 ± 0.7 |
|  | 400 | 0.4 ± 0.1 | | |
| HEp-2 | 0 | 7.1 ± 0.02 | 19X | 37 ± 1.5 |
|  | 400 | 0.4 ± 0.3 | | |
| Normal Cells | | | | |
| GM29236B | 0 | 2.5 ± 0.2 | 2X | 17 ± 1.3 |
|  | 290 | 0.8 ± 0.01 | | |
| GM2937A | 0 | 2.5 ± 0.3 | 3X | 15 ± 3.2 |
|  | 300 | 0.9 ± 0.02 | | |
| IMR-90 | 0 | 4.2 ± 0.5 | 4X | 21 ± 2.8 |
|  | 350 | 1.0 ± 0.01 | | |

TABLE 2-continued

Decreased Topo I Activity Following Ionizing Radiation in Human Cells

| Cell Type | X-Ray Dose (cGy) | Topo I[1] Enzyme Activity | Extent of Topo I[2] Down-Regulation | % Survival[3] Enhancement |
|---|---|---|---|---|

[1]Topo I enzyme activities, defined as the loss of 60% supercoiled DNA substrate (i.e., 300 μg p36B4 plasmid) per mg protein per minute, for X-irradiated and unirradiated cells at 45 min post-irradiation were determined from the slope of the linear portion of the Topo I activity curves. Experiments were repeated three times in duplicate.
[2]Extent of down-regulation of Topo I enzyme activity following equitoxic doses of ionizing radiation was calculated by the ratio of Topo I enzyme activities of unirradiated to X-irradiated cells.
[3]Survival enhancement values were determined by performing colony forming assays and values were calculated by subtracting the survival of cells immediately following ionizing radiation (i.e., no posttreatment) from the survival of irradiated cells after 4 h recovery (33, 42).

D. Regulation of Topo I mRNA and Protein Levels After Radiation.

Northern blot analyses using $^{32}$β-labeled human Topo I cDNA revealed that Topo I mRNA levels (MW: 4.2 Kb) were unchanged in CHEF and U1-Mel cells before and after ionizing radiation. Blots were also probed for 36B4 expression and a Northern loading control was unaltered with radiation as previously observed. Since Topo I mRNA levels were not altered by radiation, we then examined changes in Topo I protein levels in CHEF and U1-Mel cells. U1-Mel and CHEF cells were treated with or without ionizing radiation, nuclear protein extracts were then analyzed on 7% SDS-PAGE gels, and Topo I protein levels were detected by Western blot analyses as previously described. Topo I protein levels in CHEF cells or in U1-Mel cells were not altered by ionizing radiation. Topo I protein levels also remained unchanged in U1-Mel cells at various times post-irradiation (450 cGy) as monitored by Western blot analyses and Topo I immunoprecipitation.

E. Topo I Down-Regulation Occurs Via ADP-Ribosylation.

The mechanism by which Topo I activity was down-regulated by radiation was then explored using inhibitors of poly (ADP-ribosyl) transferase (ADPRT), an enzyme which adds poly (ADP-ribose) units to proteins. Topo I activity is modulated by phosphorylation, which activates the enzyme at the $G_1/S$ border, and by poly (ADP-ribosylation) which inactivates the enzyme. The effects of 3-ABA and PD 128763 (hereafter called PD 1), a more potent inhibitor of ADPRT, were examined on Topo I activity following radiation. The administration of 5 μM 3-ABA or 0.5 μM PD 1 to U1-Mel cells 1 hour prior to, or for 4 hours immediately after, 400 cGy prevented the down-regulation of Topo I enzyme activity. A five hour exposure of unirradiated U1-Mel cells to 0.5 μM PD1 caused only a slight loss of viability (92±1.6% viability) of unirradiated U1-Mel cells, but decreased the survival of X-irradiated U1-Mel cells to 5±0.2%. The administration of 0.5 μM PD 1 to U1-Mel cells restored Topo I activity equivalent to that observed in unirradiated U1-Mel cells. The fact that Topo I activities were down-regulated following UV-irradiation (10 J/M$^2$) was noted, and the administration of 0.5 μM PD 1 also prevented this down-regulation.

Since no apparent shift in Topo I protein molecular weight was noted in the analyses above, changes in Topo I protein were monitored using two-dimensional gel electrophoresis and Western blot analyses in unirradiated and X-irradiated (450 cGy) U1-Mel cells. Slight shifts in both molecular weight (approximately 2–5 kDa) and isoelectric point (a shift from pI: 8.2 to pI: 8.34) of Topo I from X-irradiated U1-Mel cells were noted using several known protein spots (e.g., β-actin, alpha-tubulin), as references. These data suggest that if poly (ADP-ribosylation) by ADPRT of Topo I is responsible for its down-regulated activity, the substitution must be a mono-ADP-ribosylation, possibly at a site within Topo I which is normally phosphorylated.

Based on the aforementioned data, it appears that the 3-substituted β-lapachones interact with Topo I after exposure to irradiation, chemotherapy or any DNA damaging agent and is able to interfere with Topo I down-regulation thereby increasing DNA damaging agent lethality.

II. Novel Synthesis of 3-Substituted β-Lapachone Derivatives.

Lapachol (1) is a natural product known since 1858 and is the most abundant quinone found in the heartwood of several genera Bignonoceae. Its name is derived from the "lapacho" tree (*Tabebuia avellanedae* Lr. ex. Griseb), a tree found mainly in subtropical and tropical South America (Northern Argentina, Paraguay, and Brazil). The yellow lapachol confers its color to the wood where it is sometimes visible in yellow deposits. The structure of lapachol has been known and its antitumor properties raised considerable interest in the past, having reached the stage of clinical trials. When treated with sulfuric acid it cyclizes to β-lapachone (2a), also present in the heartwood of the lapacho tree. Lapachol can also be converted into 3-bromolapachone (2b), and the latter can be converted in a two-step sequence into 3-hydroxy-β-lapachone (2c). The alcohol group of 3-hydroxy-β-lapachone is amenable to etherification when treated with alkyl halides in dry dimethyl sulfoxide in the presence of potassium hydroxide powder. It was found that it is possible to alkylate the 3-hydroxy residue of 3-hydroxy-β-lapachone without ring opening of the β-lapachone structure by avoiding alkaline reaction media which are usually necessary in etherification or esterification procedures. It was thus possible to obtain methyl, benzyl, and allyl ethers (2d) of 3-hydroxy-β-lapachone, as well as β-ethoxycarbonyl derivatives (See Synthesis 1). In synthesis 1 and 2 R is as previously defined herein.

SYNTHESIS 1

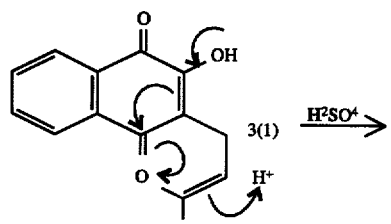

SYNTHESIS 1
-continued

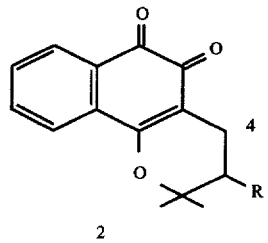

What makes this approach attractive is that lapachol is a relatively abundant natural product. In the heartwood of the abundant South American lapacho tree, its content varies between 3% (in subtropical South America) to 7% (in tropical South America). These values should be compared with those for camptothecin (0.01% in the stem wood of C. accuminata) or in taxol (0.02% in the bark of the American western yew).

When the silver salt of lapachol is alkylated (see Synthesis 2) the main products are the O-alkyl ethers of lapachol (3).

SYNTHESIS 2

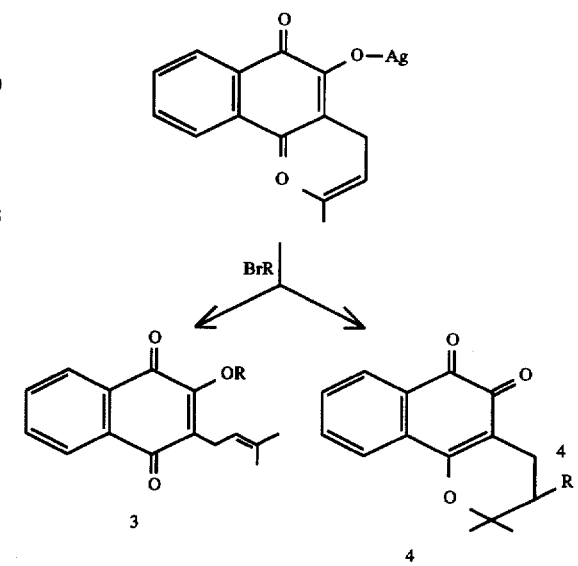

However, a very small amount of 3-substituted β-lapachones (4), obtained in 4% yield, are also formed. This side reaction takes place with the silver salt but not with the potassium or sodium salts of lapachol. The 3-substituted β-lapachones can be separated from the main reaction product 3 by extraction with a 5% bisulfite solution. Purification of 3-substituted β-lapachones requires a final chromatographic step on silica gel, using variable amounts of methanol in methylene chloride. The isolated amounts of 3-substituted-β lapachones are now ready for biological assays on Topo I enzyme assays and cell culture studies. The precise details of this general procedure are outlined below.

A. General procedures of the Synthesis of 3-O-alkyl-β-lapachone ethers

3-Hydroxy-β-lapachone-(258 mg, 1 mmol) was added to a mixture of dry and finely powdered potassium hydroxide (224 mg, 4 mmol) in 2 ml of dimethyl sulfoxide. The mixture was stirred for 10 min at 20° C., when the alkyl halide (2 mmol) was added. Stirring was continued during 30 min, water (20 ml) was then added, and the aqueous solution was then extracted with methylene chloride (3×15 ml). The pooled extracts were washed with water (3×30 ml), dried ($Na_2SO_4$) and evaporated to dryness. The residue was dissolved in a small volume of methylene chloride, adsorbed on a silica gel column prewashed with the same solvent, and the orange band was eluted with 5% methanol in methylene chloride. The eluates were evaporated to dryness, and the crystalline residue was recrystallized from ethanol.

3-Methoxy-β-lapachone (2a) was obtained in 60% yield using methyl iodide; mp 215°±–216° C.; $^1$HNMR ($CDCl_3$, ppm) 7.9 (dd, 2H), 7.6 (dd, 2H), a,b arom H; 3.4 (s,3H) $OCH_3$; 2.7–2.2 (dd,2H) $CH_2$-4; 1.90 (m, H) H-3; 1.6 (s, 3H), 1.3 (s, 3H) $CH_3$-2.

3-Benzyloxy-β-lapachone (2b) was obtained in 6% yield using benzyl bromide; mp 198°±–199° C.; 1HNMR ($CDCl_3$, ppm) 7.9 (dd)7.6 (dd); arom H; 7.3 (s, 5H) Bn; 4.6 (s, 2H) $CH_2$ Bn; 2.7 (dd)2.15 (ddd) $CH_2$-4; 1.90 (m, H) H-3; 1.6 (s), 1.3 (s) $CH_3$-2.

3-Ethoxycarbonylmethyloxy-β-lapachone (2c) was obtained in 23% yield using ethyl bromoacetate; mp 156°±–157° C.; $^1$HNMR ($CDCl_3$, ppm) 7.6 (dd)-7.6 (dd) arom H; 4.25 (q, 2H) $CH_2CH_3$; 4.10 (s, 2H) $CH_2CO$; 2.7–2.15 (dd) $CH_2$-4; 1.95 (m, H) H-3; 1.6 (s)-1.3(s) $CH_3$-2.

3-Allyloxy-β-lapachone (2d) was obtained in 55% yield using allyl bromide; mp 125°±–126° C.; $^1$HNMR ($CDCl_3$, ppm) 7.9–7.6 (dd) arom H; 5.88 (m, H) CH=; 5.30 (m, 2H) $CH_2$=; 4.0 (m, 2H) $CH_2O$; 2.77–2.15 (dd) $CH_2$-4; 2.0 (m) H-3; 1.6 (s)-1.3 (s) $CH_3$-2.

B. General Procedure of Synthesis of 3-alkyl-β-lapachone derivatives

Lapachol (1g) is dissolved in 200 ml of a 0.01N ammonium hydroxide solution with stirring and warming at 40° C. After the solid went into solution, the latter is filtered to eliminate impurities, and the excess ammonia is chased away with a stream of nitrogen so as to bring the solution to pH ca. 7.0. An aqueous solution of silver nitrate is then slowly added until the intense red color of the solution is discharged. The red precipitate is filtered, washed with distilled water, then with 95% ethanol, and finally with ether. The red silver salt (1.4 g) is dried in vacuo and grinded in a porcelain mortar. It is then suspended in 100 ml of dry ether, and a ten-fold amount of the alkyl halide is added. The mixture is stirred and heated under reflux until the red silver salt disappeared and a dark brown precipitate of silver halide was formed (reflux times varied between 0.5 hr–12 hr, depending on the halide). Conversely, the reaction can be cooled instead of heated. The silver halide was filtered and washed with ether (20 ml). The filtrates were pooled, washed with 1M sodium hydroxide (3×20 ml) to eliminate residual lapachol, then with water (5×10 ml) to neutral, dried ($Na_2SO_4$), and evaporated to dryness. The oily residue was dissolved in a small volume of chloroform, and adsorbed on a silica gel column prewashed with the same solvent. The column was washed with this eluant which eluted the O-alkyl ethers (3) as yellow bands, followed then by methylene chloride. Derivatives 3-alkyl-β-lapachol (4b) and 3-methyl-β-lapachol (4a) were eluted with the latter as orange bands; 3-ethoxy carbonyl methyl-β-lapachol (4c) was eluted with 1% methanol in methylene chloride; and 3-(2'-Hydroxyethyl)-β-lapachone (4d)) and 3'-(2'-Aminoethyl)-β-lapachone (4e) with 5% methanol in methylene chloride. The eluate containing the orange band was evaporated to dryness, and the residue crystallized from the corresponding solvent.

3-Methyl-β-lapachone (4a) was obtained in 1% yield using methyl iodide; mp 179°±180° C. (from cyclohexane); $^1$HNMR ($CDCl_3$, ppm) 7.9–7.6 (dd) arom H; 2.7–2.15 (dd) $CH_2$-4; 1.9 (m) H-3; 1.6 (s)-1.3 (s) $CH_3$-2; 1.07 (d) $CH_3$-3.

3-Allyl-β-lapachone (b)was obtained in 4% yield using allyl bromide; mp 147°±148° C. (from hexane); $^1$HNMR ($CDCl_3$, ppm) 8.0–7.6 (dd) arom H; 5.15 (m, H), 5.85 (m, 2H) vinyl; 2.8, 2.15 (dd) $CH_2$-4; 2.45 (m, $CH_2$ allyl); 1.85 (m, H) H-3; 1.6 (s, 3H), 1.3 (s, 3H) $CH_3$-2.

3-Ethoxy carbonyl methyl-β-lapachone (4c) was obtained in 1% yield using ethyl bromoacetate; mp 118°±119° (from hexane); $^1$HNMR ($CDCl_3$, ppm) 7.9–7.6 (dd), arom H; 2.8–2.15 (dd) $CH_2$-4; 4.25 (q) $CH_2CH_3$; 3.55 (s) $CH_2CO$; 1.9 (m) H-3; 1.61.4 (s) $CH_3$-2; 1.3 (q) $CH_3CH2$.

3-(2'-Hydroxyethyl)-β-lapachone (4d) was obtained in 2% yield using 2-bromoethanol; mp 205°±206° (from ethanol-water); $^1$HNMR ($CDCl_3$, ppm) 7.9–7.6 (dd) arom H; 3.8 (m, 2H) CH OH; 3.6 (b, H) OH; 2.8–2.15 (dd) $CH_2$-4; 2.0 (m) H-3; 1.70 (m), 1.60 (s), 1.40 (s) (8H) $CH_3$-2, $CH_2$-1'.

3-(2'-Aminoethyl)-β-lapachone (4e) was obtained in 1% yield using 2-bromoethylamine; mp 216°±217° C. (from ethanol water); $^1$HNMR ($CDCl_3$, ppm) 7.9–7.6 (dd) arom H; 5.0 (b, 2H) $NH_2$, 3.02 (m, 2H) $CH_2NH_2$; 2.8–2.15 (dd) $CH_2$-4; 2.0 (m) $CH_2$-1'; 1.85 (m, $H_3$); 1.6–1.3, $CH_3$-2.

This new protocol and purification synthesis for the 3-substituted compounds leads to functional yields and relative 100% purity. This synthesis is also reproducible. Therefore, this enables the use of these 3-substituted compounds as radio- and/or chemotherapy augmentors.

As used herein the term alkyl represents a straight chain or branched hydrocarbon from 1–10 carbons and all its isomeric forms such as methyl, ethyl, propyl, isopropyl, butyl, isobutyl, pentyl, etc. The aliphatic can be a saturated, unsaturated or polyunsaturated chain. Representative aliphatic groups are the paraffin, olefin and acetylene hydrocarbons and their derivatives. The term aryl denotes an organic radical derived from an aromatic hydrocarbon by the removal of a hydrogen atom. Aryl signifies a phenyl, or an alkyl, nitro, or halo-substituted phenyl group. Specifically, the term "substituted" as applied to "phenyl" refers to phenyl which is substituted with one or more of the following groups: alkyl, halogen (that is flourine, chlorine, bromine or iodine), nitro, cyano, trifluoromethyl and the like. The phenyl may be substituted with any electron donating or withdrawing groups. The term alkoxy signifies the group O-alkyl. The hydroxy group may exist as —OH or be estrified with a lipid group and have water soluble functionality. The amine may exist as a primary, secondary or tertiary amine and its derivatives. The amine may exist as —$NH_2$, —NHX where X is an alkyl from 1–10 carbons in all isometric forms, and

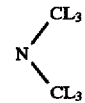

The amide may have lipid or water soluble functionality and may have an additional $CH_2$ before the hydroxy. The amide can be a primary or secondary amide in the form —$CONH_2$ or —CONHX where X is an alkyl. The amide may also be in the form of a primary or secondary amide in the form —$CH_2CH_2CONH_2$ or —$CH_2CH_2CONHX$ where X is an alkyl. The term thiol signifies —SH or —SX where X is an alkyl from 1–10 carbon atoms in all isometric forms. The halogen may be chlorine bromine, fluorine or iodine. A heteromatic is a substitute aromatic compound examples being pyridine, pyrrole, pyrimidine, imidazole, oxazole, thiophene, thiazole, morpholine, pyrazine, triazine and the like. Heterocyclics are substituted cyclic compounds.

III. Effectiveness of 3-Substituted β-Lapachone Analogues

A. Topo I Enzyme Inhibition Measurements and Induction of Apoptosis In HL60 Cells Following 3-substituted β-Lapachone Analogs.

After the synthesis of 3-substituted β-lapachone derivatives (noted above in part II), the ability of 3-substituted β-lapachone derivatives to: (a) modulate purified human Topo I; and (b) cause apoptosis using HL60 (human promyelocytic leukemia) cells, in which diagnostic 180 kbp DNA laddering and loss of intact genomic DNA are observable indicators of apoptosis.

It was demonstrated that all 3-substituted compounds, including the water-soluble 3-hydroxy-β-lapachone, inhibited Topo I in a strict, sequence-specific manner, similar to that of β-lapachone. This was shown using the previously described DNA unwinding assays found in Boothman et.al., "Inhibition of Potentially Lethal DNA Damage Repair in Human Tumor Cells by β-lapachone, an Activator of Topo I" Cancer Res. 49:605–612, (1989). The compounds were not effective Topo I inhibitors if the drug and DNA were incubated first, and the DNA unwinding reactions initiated by the addition of Topo I. The reverse was true for camptothecin derivatives. Topo I was inhibited by as little as 10 nM 3-allyl-β-lapachone and an estimated Ki of approximately 100 nM was determined. Complete inhibition of Topo I was observed at 1 μM for all 3-substituted β-lapachone compounds, including the water-soluble, 3-hydroxy-β-lapachone derivative.

For comparison, an estimated Ki of 350 nM for camptothecin to Topo I was measured under reaction conditions in which the drug was added to the DNA before the enzyme. The Topo I inhibitory effect of 3-allyl-β-lapachone was greater than β-lapachone; a Ki of 150 nM was calculated for β-lapachone.

It was discovered that β-lapachone is highly instable in air, even more so in water, and breaks down over time. There is no observance of a similar break-down reaction with the 3-substituted β-lapachone compounds in air. In addition, 3-allyl-β-lapachone was more stable in water than β-lapachone, but both compounds lose stability over time when solubilized in water or DMSO (i.e., >4 days with 3-allyl-β-lapachone; <2 days with β-lapachone). In conclusion, the results with the 3-substituted β-lapachone compounds indicate that they are very effective Topo I inhibitors which have activities greater than that of camptothecin or its analogs.

The effect of 3-substituted β-lapachone derivatives on the initiation of apoptosis using HL60 (human promyeloid leukemia) cells was then observed, where 180 kbp DNA laddering and loss of intact genomic DNA are diagnostic for the induction of apoptosis. The methodology was illustrated in Bertrand et.al., "Apoptosis and its Modulation in Human Promyelocytic HL-60 cells treated with DNA Topoisomerase I and II Inhibitors", Blood 81: 1359–1368, 1993. For all 3-substituted β-lapachone derivatives, apoptosis in HL60 cells has been observed after 4 hour treatment with 0.5–1.0 μM; complete apoptotic responses were observed at 1.0 μM and apoptosis was observed after as little as one hour after treatment. Only minor differences in effective apoptotic-inducing concentrations between 3-substituted compounds were observed. The induction of apoptosis and inhibition of Topo I activity after various concentrations of 3-substituted β-lapachone compounds compared to that occurring after β-lapachone or camptothecin exposures was then compared. For all tests of 3-substitutes-β-lapachone compounds, greater apoptosis and Topo I inhibition (at lower efficacious doses) were found compared to the β-lapachone prepared by Ciba Geigy. For each compound, the induction of apoptosis correlated well with effective Topo I inhibitory dose-responses, with the 3-substituted compounds being more effective at inhibiting Topo I and initiating apoptosis at 20–40% lower concentrations than β-lapachone. In contrast, α-lapachone or lapachol (compounds also dissolved in DMSO and used at various concentrations) did not inhibit Topo I as previously described, nor did they induce apoptosis.

B. Radiosensitization Effects of 3-Allyl-β-lapachone.

The potential radiosensitizing effects of the more stable β-lapachone derivative, 3-allyl-β-lapachone, against human radioresistant melanoma (U1-Mel) cells was then analyzed:

(i.) Optimal Concentration of 3-Allyl-β-lapachone.

The toxic effects of 3-allyl-β-lapachone on confluence-arrested human U1-Mel cells were studied. Concentrations of 3-allyl-β-lapachone up to 25 μM were less toxic to unirradiated U1-Mel cells when treated for 4 hours than similar treatments with β-lapachone. An optimal concentration range of 4–40 μM 3-allyl-β-lapachone was determined in which relatively little toxicity to unirradiated U1-Mel cells were noted. Therefore, we chose 10 μM β-lapachone as an optimal dose for continued studies. In fact, in other experiments a very large range of concentrations of 3-allyl-β-lapachone (10–40 μM) with 400 cGy appeared to be optimal, causing minimal lethal effects to unirradiated confluence-arrested U1-Mel cells, while greatly enhancing the lethality of X-irradiated U1-Mel cells.

(ii.) X-ray Dose-Response Following 3-Allyl-β-lapachone.

Using an optimal concentration of 3-allyl-β-lapachone (10 μM), its ability to enhance the lethal effects of various doses of ionizing radiation was investigated. Irradiated U1-Mel cells which were allowed to repair for 4 hours in the absence of drug increased survival as compared to cells which were not allowed to repair (i.e., cells given a no posttreatment, NPT). Addition of 3-allyl-β-lapachone immediately after radiation resulted in synergistic enhancement of lethality. Enhanced lethality of 3-allyl-β-lapachone was directly proportional to the amount of damage caused by radiation; the higher the dose of radiation the greater the enhancement. 3-Allyl-β-lapachone resulted in greater dose enhancement ratios (DERs) (3.6±0.3) compared to optimal doses of β-lapachone (at 4 μM, DER: 1.4±0.4) or camptothecin (at 4 μM, DER: 2.1±0.6) at 10% survival levels (see Table 3).

(iii.) Timing of 3-Allyl-β-lapachone Exposure for Radisensitizing Effects.

Using an optimal dose of 3-allyl-β-lapachone (10 μM) and an optimal drug exposure time of 4 hours, the effect of variations in timing of 3-allyl-β-lapachone addition was examined. When confluence-arrested U1-Mel cells were exposed to 10 μM 3-allyl-β-lapachone for 4 hours prior to radiation, no affect on survival recovery was noted. In contrast, U1-Mel cells treated with 10 μM 3-allyl-β-lapachone during or immediately after radiation resulted in synergistic enhancement of lethality. Treatment of unirradiated cells with 10 μM 3-allyl-β-lapachone did not significantly effect survival. Similar timing results with other Topo I-active drugs (i.e., camptothecin, β-lapachone, topotecan and 9-aminocamptothecin) have been described. Thus, these data are consistent with other radiosensitizing effects observed by Topo I inhibitors.

(iv.) Reversibility of 3-Allyl-β-lapachone Radiosensitization.

Confluence-arrested U1-Mel cells were unirradiated or X-irradiated (400 cGy) and exposed to 0.2% FCS-DME, 10 μM 3-allyl-β-lapachone for 4 hours. After incubation in the Topo I active drug, cells were washed and then incubated for an additional time in DME+10% FCS without 3-allyl-β-lapachone to test for reversibility of lethality. Another set of confluence-arrested U1-Mel cells were irradiated and plated immediately for survival to prevent repair (i.e., NPT). Survival levels were corrected for loss of plating efficiency due to prolonged confluence-arrest and drug exposures alone. Irradiated cells not exposed to 3-allyl-β-lapachone, but allowed to recover, increased their survival from 50% to 80% in 8 hours. X-irradiated cells exposed for 4 hours with 10 μM 3-allyl-β-lapachone did not repair after drug removal. The irreversible effects of post-irradiation exposure to 10 μM 3-allyl-β-lapachone were similar to that those observed with β-lapachone, camptothecin, topotecan or 9-aminocamptothecin.

five separate types of experiments (in accordance with the experiments listed in i–v above). For each drug: (a) the optimal drug dosage which caused radiosensitization was determined; (b) determined dose enhancement responses; (c) evaluated optimal timing of drug addition; (d) the influence of drug exposure on unirradiated and X-irradiated cells was investigated; and (e) determined whether or not drug-induced radiosensitization was reversible or irreversible. Topo I inhibitors of interest included β-lapachone, camptothecin, 3-allyl-β-lapachone, 9-aminocamptothecin, and topotecan. The results are summarized in Table 3.

Posttreatment addition of 3-allyl-β-lapachone was the most effective agent at increasing the sensitivity of radioresistant human U1-Mel cells to X-irradiation.

TABLE 3

Effect of Topo I Modulators On X-Ray-Sensitivity Of Human U1-Mel Cells[1].

| Treatment (4 Hr Post.) | Viability (%) of Unirradiated Cells | $D_q{}^3$ (cGy) | $D_o{}^3$ (cGy) | DER Values[3] 10% | 1% | 4 n |
|---|---|---|---|---|---|---|
| DME, No Post | 100 | 290 ± 8 | 210 ± 13 | 1.0 ± 0.02 | 1.1 ± 0.1 | 66 |
| DME, 0.2% FCS | 100 | 412 ± 14 | 342 ± 10 | — | — | 66 |
| 4 μM β-lapachone | 79 ± 4 | 152 ± 21 | 154 ± 8 | 1.5 ± 0.3 | 1.4 ± 0.4 | 36 |
| 10 μM 3-Allyl-β-lapachone | 89 ± 3 | 56 ± 4 | 54 ± 2 | 4.2 ± 0.2 | 3.6 ± 0.3 | 16 |
| 4 μM Camptothecin | 54 ± 2 | 132 ± 2 | 162 ± 7 | 1.8 ± 0.1 | 2.1 ± 0.6 | 22 |
| Camptothecin Derivatives | | | | | | |
| 2 μM Topotecan | 95 ± 3 | 190 ± 6 | 186 ± 4 | 1.4 ± 0.6 | 1.6 ± 0.4 | 8 |
| 4 μM Topotecan | 92 ± 4 | 127 ± 5 | 132 ± 5 | 1.6 ± 0.2 | 1.7 ± 0.3 | 8 |
| 100 μM Topotecan | 63 ± 7 | 100 ± 3 | 113 ± 2 | 2.2 ± 0.2 | 2.7 ± 0.2 | 10 |
| 10 μM 9-Amino-20(RS)- | 67 ± 5 | 110 ± 2 | 109 ± 2 | 2.5 ± 0.3 | 2.9 ± 0.4 | 12 |
| 10 μM 10,11-Methylonedioxy- | 62 ± 7 | 345 ± 3 | 254 ± 5 | 1.2 ± 0.2 | 1.4 ± 0.1 | 8 |
| 100 μM 9-Glycinamido-20(RS)- | 61 ± 3 | 352 ± 4 | 278 ± 6 | 1.1 ± 0.1 | 1.4 ± 0.4 | 8 |
| 10 μM 20-Amino-20(RS)-Deoxy(RS) | 64 ± 3 | 210 ± 5 | 197 ± 8 | 1.4 ± 0.6 | 1.8 ± 0.3 | 8 |

3-allyl-β-lapachone administered at 10 μM demonstrated greater dose enhancement ratios (DERs) (3.6 ± 0.3) compared to optimal doses of β-lapachone (at 4 μM, DER: 1.4 ± 0.4) camptothecin (at 4 μM, DER: 2.1 ± 0.6), Topotecan (at 10 μM, DER: 2.3 ± .02), and 9-aminocampotecin (at 10 μM, DER:2.9 ± 0.4) These data indicate that 3-substituted β-lapachone derivatives are more effective radiosynthetizers than camptothecin derivatives or β-lapac (v.) Kinetics of Radiosensitization by 3-Allyl-β-lapachone.

The optimal exposure time of a single dose of 3-allyl-β-lapachone (10 μM) that could enhance the efficacy of radiation was then determined. U1-Mel cells were X-irradiated (400 cGy) and allowed to repair in the absence of presence of 10 μM 3-allyl-β-lapachone. A set of X-irradiated U1-Mel cells were trypsinized and replaced immediately after radiation to determine the survival of cells not allowed to repair (i.e., NPT). Longer exposure times (i.e., 4–10 hours) of unirradiated U1-Mel cells to 3-allyl-β-lapachone did not enhance cytotoxicity. An exposure time of 4–6 hours was optimal.

C. Comparison of Topo I-active Drugs to Potentiate Ionizing Radiation Lethality.

Several Topo I modulating drugs were collected (some of which are currently in clinical trials) and used to perform IV. Inhibition of HIV-Related Reverse Transcriptase Activity By β-Lapachone The effects of Topoisomerase I (Topo I) inhibition caused by β-lapachone on the activity of HIV-related reverse tranproscriptase activity. In these reactions, reverse transcriptase is measured by the level of incorporation of (3H) dCTP into cDNA by the enzyme using a poly A⁺ mRNA as substrate. Reactions were prepared containing increasing β-lapachone concentrations, with or without the administration of Topo I. cDNA resulting from the reaction products were then analyzed by trichloroacetic acid (TCA) precipitation onto glass fiber filters. Radioactive cDNA resulting from the reverse transcriptase reaction was then measured via liquid scintillation counting. The higher the cpm on the glass fiber filters, the higher the enzyme activity. The results are demonstrated below:

TABLE 5

| Condition* | cpm On Glass Fiber Filter | |
|---|---|---|
| 1. AMV Control+ | 57,166 | ±9,242 |
| 2. AMV + 4 μM β-lapachone | 61,812 | ±6,259 |
| 3. AMV + 10 μM β-lapachone | 67,942 | ±15,969 |
| 4. AMV + 50 μM β-lapachone | 44,838 | ±2,956 |
| 5. AMV + 100 μM β-lapachone | 59,358 | ±8,616 |
| 6. AMV + Topoisomerase I (Topo I) | 14,375 | ±2,342 |
| 7. AMV + Topo I + 4 μM β-lapachone | 14,783 | ±6,351 |
| 8. AMV + Topo I + 10 μM β-lapachone | 10,092 | ±1,862 |
| 9. AMV + Topo I + 50 μM β-lapachone | 9,431 | ±4,458 |
| 10. AMV + Topo I + 100 μM β-lapachone | 7,245 | ±1,811 |
| 11. No Addition Control (Background) | 3,069 | ±1,235 |

*AMV was used at 1 unit/reaction.
+DMSO was used at a concentration equivalent to those used in β-lapachone treatments.

The results indicate that β-lapachone does not influence the enzymatic activity of AMV reverse transcriptase alone. In contrast, addition of Topo I caused a decrease in reverse transcriptase activity, which is then greatly augmented by the concomitant addition of β-lapachone. This decrease by Topo I alone could be due to the rather high levels of Topo 1 (3 units/reaction) used in the reaction conditions. The results on the inhibition of reverse transcriptase by β-lapachone, only in the presence of Topo I, are consistent with previous results which demonstrated that β-lapachone inhibits this enzyme and prolongs the life of Rous sarcoma virus infected chickens (Schaffner-Sabba K., Schmidt-Ruppin KH. Wehrli W, Schuerch AR, and Wasley JWF. "β-lapachone: Synthesis of Derivatives and Activities in Tumor Models.," J. Med. Chem 27: 990–994, 1984). Since 3-substituted-β-lapachone derivatives cause enhanced Topo I inhibition, it seems reasonable to assume that these derivatives will be effective reverse transcriptase inhibitors and prevent the replication of the HIV virus.

I claim:

1. A compound having the structure:

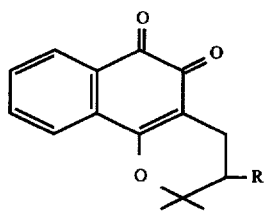

wherein R is allyloxy, ethoxycarbonylmethyl, or ethoxycarbonylmethyl.

2. The compound of claim 1 wherein said compound is 3-ethoxycarbonylmethyl-β-lapachone.

3. The compound of claim 1 wherein said compound is 3-ethoxycarbonylmethyloxy-β-lapachone.

4. The compound of claim 1 wherein said compound is 3-allyloxy-β-lapachone.

5. A method of enhancing the lethality of a DNA damaging agent in neoplastic cells comprising the steps of:
   a. exposing a neoplastic cell to a DNA damaging agent, and
   b. subjecting the neoplastic cell to a 3-substituted 3-lapachone selected from the group consisting of

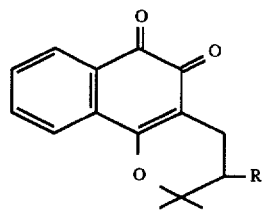

wherein R is allyloxy, $-O-(CH_2)_n-R_1$, or $(CH_2)_n-R_1$ where n is an integer from 0–10 and $R_1$ is hydroxy, an alkIcarboxy, a heteroaromatic, a heterocyclic, an amine, a thiol, an amide, or a halogen.

6. The method of claim 5 wherein said DNA damaging agent is radiotherapy.

7. The method of claim 5 wherein said DNA damaging agent is chemotherapy.

8. The method of claim 5 wherein said 3-substituted β-lapachone is 3-allyl-β-lapachone.

9. The method of claim 5 wherein said 3-substituted β-lapachone is 3-ethoxycarbonylmethyl-β-lapachone.

10. The method of claim 5 wherein said 3-substituted β-lapachone is 3-(2'-Hydroxyethyl)-β-lapachone.

11. The method of claim 5 wherein said 3-substituted β-lapachone is 3-methyl-β-lapachone.

12. The method of claim 5 wherein said 3-substituted β-lapachone is 3-(2'-aminoethyl)-β-lapachone.

13. The method of claim 5 wherein said 3-substituted β-lapachone is 3-hydroxy-β-lapachone.

14. The method of claim 5 wherein said 3-substituted β-lapachone is 3-methoxy-β-lapachone.

15. The method of claim 5 wherein said 3-substituted β-lapachone is 3-benzyloxy-β-lapachone.

16. The method of claim 5 wherein said 3-substituted β-lapachone is 3-ethoxycarbonylmethoxy-β-lapachone.

17. The method of claim 5 wherein said 3-substituted-β-lapachone is 3-allyloxy-β-lapachone.

18. A method of chemotherapy comprising the step of: exposing a neoplastic cell to a 3-substituted-β-lapachone in sufficient amounts to induce cell death.

19. The method of claim 18 wherein the 3-substituted β-lapachone is present in an amount of from about 0.7 μM to about 10 μM.

20. The method of claim 18 wherein the neoplastic cell is selected from human neoplastic melanoma, lung, breast, prostate, leukemia and colon cells.

21. The method of claim 18 wherein said 3-substituted β-lapachone has the structure:

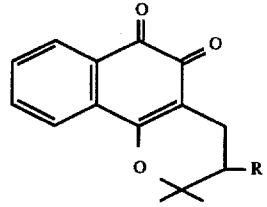

wherein R is allyloxy, $-O-(CH_2)_n-R_1$, or $(CH_2)_n-R_1$ where n is an integer from 0–10 and $R_1$ is hydroxy, an alkylcarboxy, a heteroaromatic, a heterocyclic, an amine, a thiol, an amide, or a halogen.

22. The method of claim 18 wherein said cell death is via apoptosis.

23. The method of claim 18 wherein said cell death is via necrosis.

24. The method of claim 18 wherein said 3-substituted-β-lapachone is 3-allyl-β-lapachone.

25. The method of claim 18 wherein said 3-substituted-β-lapachone is 3-ethoxycarbonylmethyl-β-lapachone.

26. The method of claim 18 wherein said 3-substituted-β-lapachone is 3-(2'-hydroxyethyl)-β-lapachone.

27. The method of claim 18 wherein said 3-substituted-β-lapachone is 3-methyl-β-lapachone.

28. The method of claim 18 wherein said 3-substituted β-lapachone is 3-hydroxy-β-lapachone.

29. The method of claim 18 wherein said 3-substituted-β-lapachone is 3-methoxy-β-lapachone.

30. The method of claim 18 wherein said 3-substituted-β-lapachone is 3-benzyloxy-β-lapachone.

31. The method of claim 18 wherein said 3-substituted-β-lapachone is 3-ethoxycarbonylmethoxy-β-lapachone.

32. The method of claim 18 wherein said 3-substituted-β-lapachone is 3-allyloxy-β-lapachone.

* * * * *